United States Patent [19]
Tokosh et al.

[11] 4,275,013
[45] Jun. 23, 1981

[54] NOVEL PROCESS FOR THE PREPARATION OF SALTS OF ALKANESULFONIC ACIDS

[75] Inventors: Richard Tokosh, Saddle Brook; Joseph Barillo, Glen Rock; Warren Urban, River Vale, all of N.J.

[73] Assignee: Lever Brothers Company, New York, N.Y.

[21] Appl. No.: 683,458

[22] Filed: May 5, 1976

Related U.S. Application Data

[63] Continuation of Ser. No. 535,771, Dec. 23, 1974, abandoned, which is a continuation of Ser. No. 334,514, Feb. 21, 1973, abandoned.

[51] Int. Cl.³ ............... C07B 13/00; C07C 143/02
[52] U.S. Cl. ........................ 260/504 R; 260/504 A; 260/513 B
[58] Field of Search ............ 260/513 B, 504 R, 504 A

[56] References Cited

U.S. PATENT DOCUMENTS

| | | | |
|---|---|---|---|
| 2,504,411 | 4/1950 | Harman | 260/513 B |
| 2,653,970 | 9/1953 | Fessler | 260/513 B |
| 2,793,229 | 5/1957 | Blaser et al. | 260/513 B |
| 2,806,876 | 9/1957 | Blaser et al. | 260/513 B |
| 3,168,555 | 2/1965 | Clippinger et al. | 260/513 B |
| 3,306,931 | 2/1967 | Adams et al. | 260/513 B |

*Primary Examiner*—Alan Siegel
*Attorney, Agent, or Firm*—James J. Farrell; Melvin H. Kurtz; Irving N. Feit

[57] ABSTRACT

A process for the preparation of salts of alkanesulfonic acids, hereinafter referred to as alkanesulfonates, by the addition of alpha olefins to bisulfite in a cosolvent system consisting of water and an organic hydroxyl-containing compound in the presence of a free radical initiator.

17 Claims, No Drawings

NOVEL PROCESS FOR THE PREPARATION OF SALTS OF ALKANESULFONIC ACIDS

This is a continuation, of application Ser. No. 535,771, filed Dec. 23, 1974 now abandoned which is a continuation of Ser. No. 334,514, filed Feb. 21, 1973 now abandoned.

BACKGROUND OF THE INVENTION

1. Field of the Invention

It is well known in the art that alkanesulfonates can be prepared by adding bisulfite to an olefin in a liquid reaction medium in the presence of a free radical initiating agent. Two methods of preparing alkanesulfonates have been cited in the past where (1) all the reactants are charged together, hereinafter referred to as "Dump In" or "Charged Together" method and (2) where a prepared sodium bisulfite solution is added continuously, over a two to four hour period, to a solution comprising an alpha olefin, cosolvent, and free radical initiator. A discussion of the prior art relative to the above-mentioned processes will be discussed in detail elsewhere in the specification. Needless to say, the prior art in varying degrees discusses the importance of controlling such things as pH, reflux conditions, maintenance of no more than two phases of reaction mixture, and so forth. Applicants know of no process, however, that will be practical for the production of alkanesulfonates where the olefin is added to a bisulfite solution consisting essentially of cosolvent and free radical initiator. Contrary to the teachings of the prior art, applicants have found that alkanesulfonates can be prepared by adding alpha olefins to a sodium bisulfite solution comprising water and an aliphatic organic hydroxyl-containing compound, such as isopropanol, in the presence of a free radical initiator. Stated succintly, as opposed to the prior art processes enumerated above, the instant process is accomplished by the addition of olefin to a bisulfite solution.

The novel and unobvious aspects of the instant invention can be more readily appreciated and understood by a discussion of the knowledge of the art heretofore.

2. The Prior Art

U.S. Pat. No. 2,398,426

Discloses the preparation of alkanesulfonic acids and their salts from salts of sulfurous acid and olefins of less than four carbon atoms. The method is accomplished by reacting the olefin with a water-soluble salt of sulfurous acid at a temperature of 90° C. to 200° C. and a pressure of at least 400 atmospheres. More specifically, all reactants, exclusive of the olefin, are charged to a vessel, the vessel closed and mounted on a shaker machine. The system is pressured with sufficient olefin to give approximately the required pressure at the desired reaction temperature.

U.S. Pat. No. 2,504,411

Discloses the preparation of alkanesulfonates using peroxide catalysts and polar organic mutual solvents selected from alcohols, cyclic diethers, and organic amines. The method is accomplished by heating in a closed vessel the olefin and bisulfite in the presence of the peroxide and mutual solvent at a temperature of from 50° C. to 200° C.

U.S. Pat. No. 3,084,186

Discloses the preparation of alkanesulfonates whereby not more than two liquid phases, i.e. an oil phase and an aqueous phase, are maintained by a controlled gradual addition of bisulfite ion at a rate approximately equal to its rate of consumption during the course of reaction until at least the stoichiometric amount of bisulfite ion has reacted with the olefin. The method is accomplished by introducing olefin and bisulfite ion into the reaction zone in the presence of polar solvent and reaction initiating agent under sulfitation conditions, in a mol ratio of bisulfite ion to olefin of about 0.05 to 0.25 whereby a two liquid phase reaction medium is formed, further introducing into the reaction zone during the course of reaction additional bisulfite ion at a rate such as to maintain an amount of unreacted bisulfite ion in the reaction zone within the range of 0.05 to 0.25 mole per mole of original olefin introduced and continuing the addition of bisulfite ion at least until the stoichiometric amount of bisulfite has been reached.

U.S. Pat. No. 3,275,681

Discloses the preparation of alkanesulfonates using as catalyst a combination of a peroxide and an organometal salt. The method is accomplished by dissolving the bisulfite in water, the olefin in an organic solvent along with the peroxide and organometal. The two solutions are mixed and stirred for the period of time required to give the desired yield.

U.S. Pat. No. 3,522,297

Discloses the preparation of alkanesulfonates wherein the process is accomplished by preaerating the olefin with an oxygen containing gas and then reacting a non-interfering bisulfite with the preaerated olefin.

U.S. Pat. No. 3,541,140

Discloses the separation of alkanesulfonate product from the reaction mixture by maintaining a critical alcohol to water ratio and a critical temperature range.

U.S. Pat. No. 3,558,693

Discloses the preparation of a quaternary ammonium alkylsulfonate wherein a tetraalkylammonium bisulfite is used as the source of bisulfite ions. This bisulfite ion is formed in situ from a reaction mixture comprising anhydrous solvent, sulfur dioxide, quaternary ammonium hydroxide. The olefin and initiator are added to this mixture. All reactants are used from the beginning and in a single addition.

U.S. Pat. No. 3,644,499

Discloses the stabilization of organic sulfonates, prepared by conventional means, by the use of a combination of water, oxygen and an alkaline compound.

SUMMARY OF THE INVENTION

As aforestated, it has now been found that alkanesulfonates can be prepared by adding an alpha olefin to a sodium bisulfite solution comprising water, an organic hydroxyl compound and a free-radical initiator. Specifically, in this process the alpha olefin, containing an olefin-soluble free-radical initiator, is continuously added to a sodium bisulfite solution, at reflux, over a two hour period. This is especially surprising because by such an addition, i.e. small increments of alpha olefin to a huge predominance of sulfitation reagent, one would expect a high amount of the undesirable sulfinate-sulfonate and disulfonates. The reaction is more graphically illustrated as follows:

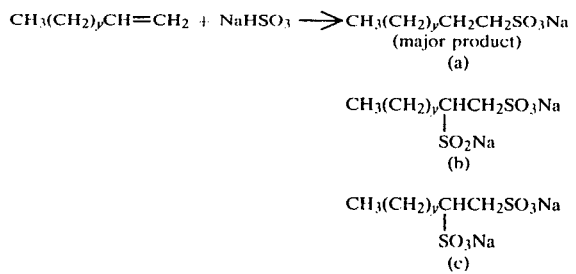

(a) (major product)

CH$_3$(CH$_2$)$_y$CHCH$_2$SO$_3$Na
|
SO$_2$Na
(b)

CH$_3$(CH$_2$)$_y$CHCH$_2$SO$_3$Na
|
SO$_3$Na
(c)

where y=7 and 11 present at about 50% of each. Stated otherwise one skilled in this art would expect a predominance of the products exemplified by (b) and (c) rather than the predominance of alkanesulfonate as is herein accomplished. In short, analytical data show that this process will produce a reaction mixture of alkanesulfonates similar to that prepared by the known sodium bisulfite addition method.

The addition of the olefin, containing the initiator system, to the sodium bisulfite-cosolvent mixture results in several advantages heretofore not attainable in the art, i.e. (a) continuous addition of the catalyst simultaneously with the olefin addition, (b) minimization of an oxidation of the sodium bisulfite solution prior to and during the course of reaction and (c) obtention of a product lower in inorganic content. The continuous addition of catalyst results in a significant economic benefit because of the expense of peroxide catalyst. This is because the inherent "cage effect", which results from prior art methods, is greatly minimized and therefore less initiator is needed. The instant mode of catalyst addition also results in a marked reduction of undesirable byproducts, e.g. tetramethylsuccionitrile, when azobis(isobutyronitrile) (AIBN) is used. Additionally, the fact that the bisulifite is in the reaction medium from the very beginning avoids the necessity of conducting the reaction under an inert atmosphere, i.e. nitrogen. This is because the alcohol vapors from the cosolvent will prevent air from reaching the bisulfite. The ultimate benefit is the reduction in formation of inorganic material, i.e. sodium sulfate. An additional advantage and cost savings is the fact that smaller vessels and carbon-steel, rather than stainless steel, equipment may be used to store the olefin which is subsequently added to the reaction vessel.

The object of the instant invention is to provide a process wherein an alkanesulfonate can be prepared without the problems hereinbefore encountered in the art. A further object is to prepare an alkanesulfonate in high yield, of high purity, and exhibiting a high degree of biodegradability as well as excellent surfactant properties. A still further object is to prepare an alkanesulfonate compound of sufficient purity for ultimate use in high proportions in a toilet bar.

According to the prior art, the olefinic materials used in the preparation of sulfonation products, by the addition of bisulfite ion to olefin, can be any of a broad class of unsaturated compounds regardless of the position of the double bond or bonds and the molecular structure or nature of the unsaturated compound. This invention, however, is specifically applicable to olefinic materials having a terminal olefinic bond, that is alpha olefins, which can be characterized as being essentially alpha-monoolefins of essentially acyclic straight-chain or branched chain 1-olefins of 5 to 30 carbon atoms. The branched chain olefins that may be used in the instant process are those which have no branching on the 1 or 2 carbon of the vinyl group. Long chain vinylidene compounds with a methyl or ethyl on the 2 carbon may also be used. However, vinylidine compounds with substituents above ethyl as well as either trans-isomers or trisubstituted isomers, straight or branched chain, are inoperable in the instant invention. The instant process is applicable to individual olefins of the above-defined class or mixtures thereof. The above-defined olefin may contain, in limited amounts, impurities, contaminants, and other olefins such as internal or secondary olefins. The presence of these "other olefins" is not detrimental because they react to such a limited extent that they do not interfere with the sulfitation of the above-described normal 1-olefins.

The instant process, as will be later exemplified in greater detail, is conducted by initially dissolving, for example sodium metabisulfite, in water with agitation to form sodium bisulfite. The pH of this solution is adjusted to about 5.5 with a base, preferably NaOH. This solution is added to the organic hydroxyl compound viz. alcohol plus 25% of the t-butyl perbenzoate catalyst and heate to reflux. The olefin, plus the balance of the catalyst, is added to the agitating bisulfite/organic hydroxyl compound mixture over a two hour period. After the olefin/catalyst addition, the mixture is refluxed, while maintaining the pH at approximately neutral by sparging SO$_2$ into the reaction mixture, for an additional two hours and the product is subsequently recovered.

As aforestated the olefin, which contains an oil soluble free radical initiator, is added to the refluxing sodium bisulfite cosolvent mixture. This mixture comprises sodium bisulfite, water, and a polar solvent comprising an organic hydroxyl-containing compound, such as an alcohol. The term polar solvent, as used herein, refers to a lower molecular weight aliphatic organic hydroxyl-containing compound of from 1 to 6 carbon atoms, i.e. C$_1$-C$_6$. The preferred and most normally used polar solvents are alcohols such as methanol, ethanol, and isopropanol. Also included in this class of solvents are such things as diols, polyols, polyhydroxy ethers of 1 to 6 carbon atoms.

It may be desirable to include in the cosolvent an additional faster initiator to help rapid production of free radical species in the reaction mixture. This can be accomplished by the use of co-initiators having differing half-lives. An illustration of this is as follows: benzoyl peroxide—2.1 hours, t-butyl perbenzoate—150 hours, di(t-butyl peroxide)-1000 hours, t-butyl peroxymaleic acid—12 hours, 2,2'azobis(isobutyronitrile)—0.53 hours. (These half-lives are at 85° C.). The initiator having a shorter half-life will boost the reaction, thus decreasing the residence time of the reactants where a single catalyst is used. Furthermore, this insures a smoother reaction because when the faster initiator has dissipated, the slower initiator has, in the interim, become activated and thus insures continuance of the reaction to completion. Some types of reaction initiating agents that can be employed for this reaction are molecular oxygen, NaOCl, inorganic oxidizing compounds, such as inorganic peroxides, e.g. H$_2$O$_2$, Na$_2$O$_2$; organic peroxides, such as benzoyl peroxide and peracetic acid. The preferred peroxides are organic peroxides in which the peroxy group is attached to at least one tertiary carbon atom, such as tertiary-butyl perbenzoate, tertiary-butyl pertoluate, 2,2-bis-(t-butyl-peroxy)butane, ditertiary-butyl peroxide, tertiary-butyl perphthalates (ortho compound) and t-butyl peroxymaleic acid. In addition to the aforementioned, azobisisobutyronitrile (AIBN) was also found to be effective alone as well as in combination with other initators. As a matter of fact any of the above-mentioned peroxides may be used singly or in combination when the boosting effect is desired.

As previously suggested, the best source of bisulfite ion is sodium bisulfite. However, other sources of bisulfite ion may also be employed. This includes sodium metabisulfite, ammonium bisulfite, calcium bisulfite, potassium bisulfite and magnesium bisulfite. The definition of alkali metal bisulfite is intended to include the ammonium bisulfite of the instant specification.

Although pH is not critical to the invention and various ranges of pH have been found to be beneficial to the formation of alkanesulfonate, it has been found that maintenance of pH in the aqueous phase during reaction is advantageous and represents an important refinement feature of the invention. Specifically applicants have found that maintaining a pH range of about 4 to about 9, preferably in the range of about 6 to about 8, most preferably at a pH of 6.9±0.2, produces high purity alkanesulfonates in excellent yields. This pH may be maintained by either (a) sparging with $SO_2$, (b) adding mineral acids (such as sulfuric, phosphoric, nitric, and hydrochloric acids), (c) adding organic acids, such as fatty acids containing from 8 to 16 carbon atoms, and (d) adding combinations of the above to the bisulfite solution during the reaction. $SO_2$ is most preferred because in addition to maintaining pH it also serves to replenish consumed bisulfite ion. The reason for keeping the pH below 9 is because above this pH the desired bisulfite ion is largely neutralized to sulfite which is nonreactive, while below a pH of about 4 the bisulfite is converted to sulfurous acid which can decompose to $SO_2$ and water. Within the defined pH range less difunctional sulfur compounds are formed. It may also be necessary to utilize alkaline reagents to maintain the pH. Practically any alkaline reagent may be used, e.g. basic metal oxides, basic metal hydroxides, basic nitrogen compounds such as CaO, MgO, NaOH, KOH, $Mg(OH)_2$, $NH_3$, amines etc. The amount employed need be just the amount required to obtain and maintain the desired pH. A more comprehensive discussion of pH effects may be found in an article by Norton et al, J. Org. Chem., 33 No. 11, Nov. 1968 (pp 4158–4165).

The temperature employed during reaction can vary widely, from a low of about 50° C. to a high of about 200° C. For the preferred organic peroxide initiators and also AIBN, temperatures ranging from about 75° C. to 100° C. are suitable.

It is also often advantageous to conduct the reaction in the presence of a small amount of alkanesulfonate, i.e., a "heel", as from a preceding run, up to about 15 mole percent.

The molar ratio of alkali or alkaline earth metal bisulfite to olefin will vary from about 0.1/1.6 to about 1.0/1.6 mole. For example, the reaction will proceed at a level of about 0.1/1.6 mole of olefin to bisulfite in the bisulfite reaction mixture, olefin is continuously added over a period of 1½ to 2 hours until the final molar ratio is about 1.0/1.6. A preferred ratio is that of 1.0 moles of olefin to 1.2 moles of bisulfite ion.

The level of initiator present in the bisulfite reaction mixture may range from 0% to 100% of total initiator to be used. Optimally, about 1–25% of the catalyst to be used will be present in the bisulfite reaction mixture prior to the addition of the olefin. Although the reaction will proceed with 0% catalyst in the bisulfite mixture, the rate of alkanesulfonate formation will be very slow. Ideally, it is desired to have about 20–25% of catalyst present in the bisulfite reaction mixture and to add the remainder of the catalyst simultaneously with the olefin.

In any event, the ratio of total moles of catalyst to total moles of olefin will range from 0.005 to 0.10, i.e. from 0.5 to 10 mole percent, preferably from 0.008 to 0.030 and most preferably from 0.011 to 0.025. It has also been found that the reaction is enhanced by the use of fresh catalyst. The enhancement is reflected in the use of lower catalyst levels and also in shorter reaction times.

The ratio of organic hydroxyl containing compound to water may vary from about 4:1 to 1:9, preferably from 3:2 to 7:3.

As the reaction proceeds to completion, a single-phase water-white liquid is formed. Prior to completion, depending upon how the catalyst is added, there may be two or three phases. The single-phase water-white liquid will contain the alkanesulfonate of the instant invention as well as disulfonate, sulfinate-sulfonate product, unreacted olefin, hereinafter referred to as "nondetergent organic matter" (NDOM), and inorganic salts, which are insoluble in dimethylsulfoxide (DMSO), hereinafter referred to as DMSO insolubles. The amount of alkanesulfonate is determined by measuring the amount of unreacted olefins (NDOM) and total solids. The total solids include both the inorganic material (DMSO insolubles) and sulfonate products. The difference between total solids and DMSO insolubles yields the amount of sulfonates, i.e. active material. The yields of active material, based on the amount of unreacted olefin, range from 65% to 95% depending upon how the alkanesulfonate is processed.

As previously stated, one of the primary purposes of the product of this invention is as a constituent of toilet bars. A brief discussion illustrating this use may be helpful at this point.

Normally alkenesulfonates mady by adding $SO_3$ to an alpha olefin, although being much harder than alkylbenzenesulfonates, become very sticky when small percentages of water are incorporated in a formed detergent bar. As a consequence, bars made from these materials are also very difficult to process in the usual soap-making equipment, and additionally have a tacky after-feel on the hands and also exhibit a wear rate which is extremely high, and thus are undesirable notwithstanding the fact that the later evolved is of excellent quality.

The alkenesulfonates, particularly in the $C_8$–$C_{18}$ molecular weight range have also been suggested for use in detergent compositions. These materials are hard, at least as mild as soap, and will tolerate up to 25% water without becoming sticky.

An inexpensive, synthetic detergent toilet bar, utilizing the alkanesulfonate of the instant invention, is provided having superior lathering properties under all water conditions, which is mild and has a soap-like after-feel to the skin, which is non-mushing under conditions of use and is readily processed with conventional soap-making equipment by incorporating in selected proportions an alkanesulfonate containing 8–18 carbon atoms in the alkyl chain or a mixture of alkanesulfonates averaging 8–18 carbon atoms in the alkyl chain, superfatting agent comprising natural or synthetic fatty acids. The bar so provided has a composition comprising, based on the actives present, of about 10% to about 90%, preferably about 40–80%, by weight of the alkanesulfonate, preferably the alkali metal or magnesium salt, about 5% to about 35% of a natural or a synthetic fatty acid, and 5% to about 30% of a suds booster, and based on the total weight of the bar, 5% to about 25% water.

An additional feature that may be utilized when preparing toilet bars from the alkanesulfonates of this invention is to mix with said alkanesulfonates such other items as perfumes, dyes, or colorants, germicidal substances, emollients, inorganic builders (if desired), opacifiers, and hardeners. After all the ingredients are mixed, the water-solvent system is removed by processes known to the art, such as vacuum drying, distillation, flash or drum drying. Although only toilet bars have been discussed as one of the end uses of the alkanesulfonates of this invention, the product of this invention may also be used as a detergent active, suds booster, lime soap scum dispersant and as a hydrotrope.

The following Examples will illustrate further the present invention, however, not limiting the same thereto.

EXAMPLE 1

A sodium bisulfite solution is prepared by dissolving 4.2 moles sodium meta-bisulfite in 201.8 moles distilled water while agitating with a magnetic stirrer. The pH of this solution is adjusted with 50% solution sodium hydroxide until a pH of 5.5 is obtained (about 1.34 moles). This prepared sodium bisulfite solution, is added to the flask along with 40.0 moles of isopropyl alcohol and 0.05 moles tert-butyl perbenzoate catalyst. The mixture is heated to reflux.

To the agitating sodium bisulfite/alcohol/water mixture are added 6.9 moles 1:1 $C_{10}$–$C_{14}$ alpha olefin, containing 0.15 moles tert-butyl perbenzoate catalyst over a two hour period. After olefin-catalyst addition the mixture is refluxed (about 82° C.) for an additional two hours while maintaining the pH at 6.9±0.2 by sparging sulfur dioxide into the reaction mixture. The resultant mixture, at the conclusion of the reaction, contained NDOM—1.1%, total solids—26.3%, DMSO insolubles—8.0%. The conversion, basis consumed olefin, is found to be 95+%.

EXAMPLE 2

Example 1 is repeated except that 0.07 moles azobisisobutyronitrile catalyst is added to the sodium bisulfite cosolvent mixture before reflux and olefin addition. The balance of the catalyst, 0.15 moles tert-butyl perbenzoate, is added to the olefin. After two hours olefin-catalyst addition the mixture is refluxed for two hours while maintaining the pH at 6.9±0.2 with sulfur dioxide. The resultant mixture, at the conclusion of the reaction, contained 2.0% NDOM, 26.2% total solids, and 11.8% DMSO insolubles. The conversion (basis consumed olefin) is 89+%.

EXAMPLE 3

Example 1 is repeated except that 0.06 moles azobisisobutyronitrile catalyst is added to the sodium bisulfite cosolvent mixture before reflux and olefin addition. The balance of the catalyst, 0.16 moles azobisisobutyronitrile is added in periodically over the two hour olefin addition. As in Example 1 reactants are refluxed for an additional two hours, at pH 6.9±0.2. The resultant mixture, at the conclusion of the reaction, contained 2.2% NDOM, 26.1% total solids, and 7.3% DMSO insolubles.

EXAMPLE 4

Example 1 is repeated except that 0.04 moles of NaOCl is used as catalyst and tetradecene-1 is used as the olefin. The conversion is 94+% on a consumed olefin basis.

EXAMPLES 5–9

The following Examples shown in Table I illustrate the preparation of alkanesulfonates according to the process of the instant invention using varying chain lengths of olefins, varying times and varying catalyst concentrations. The catalyst used was not fresh catalyst, however.

It can be readily observed from the following Examples that there is a direct relationship between total catalyst consumed (whether mixed or not), reaction time, total solids, NDOM, and DMSO insolubles. Whenever aged catalyst is used at low levels, i.e. 0.07 moles, which is about 1 mole % based on the olefin longer reaction times are required, about 4–5 hours, in order to obtain optimal yields of total solids and acceptable levels NDOM and DMSO insolubles. There is no real upper limit on the amount of total catalyst that may be used, other than expense.

Ideally, the total reaction time should be at least two hours, i.e. one hour of addition and one hour of reflux time. When using fresh catalyst, as exemplified below, results comparable to Examples 5–9 can be achieved in this time. In any event one skilled in the art is not limited solely to fresh catalyst, but may use aged catalyst also. The precise sets of parameters and conditions can be readily determined by experimentation. The corrected actives percentage is determined by calculating the amount of DMSO in the total solids based on percent NDOM and subtracting that from the total solids: Although only $C_{10}$ and $C_{14}$ olefins are illustrated, similar results are obtained when using $C_5$ and $C_{30}$ olefins within the definition of this invention.

TABLE I

| Example No. | Olefin Chain Length | Addition Time (Hours) | Catalyst System | Reflux Time (Hours) | %NDOM | Total Solids % | DMSO Insol. | Corrected Active % |
|---|---|---|---|---|---|---|---|---|
| 5 | $C_{10}$ | 2 | 0.07m AIBN(a) 0.11m TBP(b) | 2 | 2.1 | 24.2 / 25.9(theo) | 11.2 | 21.5 |
| 6 | $C_{10}$ | 1½ | 0.07m AIBN(a) 0.04m TBP(b) | 2 | 2.0 | 23.6 / 25.9(theo) | 16.8 | 19.6 |
| 7 | $C_{14}$ | 2 | 0.08m TBP(a) 0.11m TBP(b) | 2 | 2.3 | 26.0 / 28.4(theo) | 9.8 | 23.4 |
| 8 | $C_{10}$–$C_{14}$ | 2 | 0.04m TBP(a) 0.08m TPB(b) | 2 | 1.6 | 25.3 / 26.6(theo) | 19.4 | 20.4 |

TABLE I-continued

| Example No. | Olefin Chain Length | Addition Time (Hours) | Catalyst System | Reflux Time (Hours) | %NDOM | Total Solids % | DMSO Insol. | Corrected Active % |
|---|---|---|---|---|---|---|---|---|
| 9 | $C_{10}-C_{14}$ | 2 | 0.04m TBP(a) 0.08m TBP(b) | 2 | 1.0 | 25.7 / 26.6(theo) | 8.2 | 23.6 |

(a) amount of catalyst initially charged to reactor
(b) amount of catalyst added simultaneously with the olefin
(theo) refers to theoretical yield
(AIBN) refers to azobis(isobutyronitrile)
(TBP) refers to tertiary-butyl-perbenzoate

EXAMPLES 10-17

The following Examples shown in Table II show the process of the instant invention using fresh catalyst. The procedure, employing some slight modifications, as is follows: 4.2 moles of sodium metabisulfite is dissolved in 3630 grams of water, 1.34 moles of 50% NaOH is added to the solution resulting in a pH of 5.5-5.65. To the reactor flask containing said solution is added 2400 grams of isopropanol and 0.031 moles of AIBN catalyst. The reaction mixture is heated to reflux (82°-83° C.). 3.45 moles of $C_{10}$, $C_{14}$, $C_{10}-C_{14}$ alpha olefin (where applicable) is added over a one-hour period containing 0.026 mole of t-butyl perbenzoate catalyst. At the end of the one hour addition 0.012 mole of AIBN is added to the reaction mixture. The addition is continued for one hour with another 3.45 moles of olefin containing 0.010 moles of t-butyl perbenzoate. The pH is maintained at 6.8-7.0 by the addition of $SO_2$. The reaction mixture is then refluxed for an additional two hours. The reaction mixture is discharged and analyzed at the end of the period. The analysis used is the standard Hyamine titration. The corrected actives percentage is determined by calculating the amount of DMSO in the total solids based on percent NDOM and subtracting that from the total solids.

single catalyst system rather than a mixed catalyst system is used. In the AIBN run a total of 0.07 moles of catalyst is used in increments of 0.018 moles and 0.052 moles. In the t-butyl perbenzoate run a total of 0.072 moles are used in increments of 0.026 mole, 0.026 mole, 0.010 mole and 0.010 mole. The analyses are the same as in the previous Examples, i.e. Table II.

At the start of the olefin addition the reaction mixture pH is 6.15-6.2. After the addition of olefin for one hour and 25 minutes the pH rose to 7.0-7.10 and a clear water-white solution is obtained. $SO_2$ should be introduced at this point in a slow steady stream to maintain the pH at approximately neutral.

TABLE III

| Example No. | Olefin Chain Length | Addition Time (Hours) | Reflux After Addition | Catalyst System | % NDOM | Total % Solids | % DMSO Insol. | Corrected Active % | Active Hyamine |
|---|---|---|---|---|---|---|---|---|---|
| 18 | $C_{10}-C_{14}$ | 2 | 2 | 0.07m AIBN | 1.2 | 25.3 | 9.1 | 23.0 | 21.8 |
| 19 | $C_{10}-C_{14}$ | 2 | 3 | 0.072m TBP | 2.4 | 25.0 | 10.0 | 22.5 | N.D. |

N.D. = not determined

EXAMPLE 20

The following table illustrates the use of alpha olefins of varying chain lengths as well as different solvents. The procedure utilized is in accordance with Example 1. The reflux times and temperatures will, of course, vary with the particular solvents used. The adjustment of either of these parameters is within the skill of the art.

TABLE II

| Example No. | Olefin Chain Length | Addition Time (Hours) | Reflux After Addition | Catalyst System | % NDOM | Total % Solids | % DMSO Insol. | Corrected Active % | Active Hyamine |
|---|---|---|---|---|---|---|---|---|---|
| 10 | $C_{10}-C_{14}$ | 2 | 1 | 0.043m AIBN 0.036m TBP | 1.6 | 25.1 | 8.4 | 23.0% | N.D. |
| 11 | $C_{10}-C_{14}$ | 2 | 2 | 0.043m AIBN 0.036m TBP | 1.1 | 25.3 | 8.9 | 23.0 | 23.0% |
| 12 | $C_{10}-C_{14}$ | 2 | 1 | 0.043m AIBN 0.036m TBP | 1.6 | 25.4 | 10.3 | 22.8 | N.D. |
| 13 | $C_{10}-C_{14}$ | 2 | 2 | 0.043m AIBN 0.036m TBP | 1.1 | 25.9 | 8.5 | 23.7 | 23.2 |
| 14 | $C_{10}-C_{14}$ | 2 | 2 | 0.043m AIBN 0.036m TBP | 0.5 | 27.5 | 11.4 | 24.4 | 23.2 |
| 15 | $C_{10}$ | 2 | 2 | 0.043m AIBN 0.036m TBP | 2.3 | 24.2 | 8.4 | 22.2 | 20.9 at mw 265 |
| 16 | $C_{14}$ | 2 | 2 | 0.043m AIBN 0.036m TBP | 1.7 | 27.2 | 8.3 | 24.9 | N.D. |
| 17 | $C_{14}$ | 2 | 3 | 0.043m AIBN 0.036m TBP | 1.4 | 27.6 | 7.5 | 25.5 | N.D. |

N.D. - not determined

EXAMPLES 18-19

The following Examples shown in Table III are carried out in accord with the present invention wherein a

TABLE IV

| Olefin Chain Length | Solvent | Temperature | % Yield (Consumed Olefin Basis) |
|---|---|---|---|
| $C_6$ | ethylene- | 60-63° C. | 85 |

TABLE IV-continued

| Olefin Chain Length | Solvent | Temperature | % Yield (Consumed Olefin Basis) |
|---|---|---|---|
| (a)$C_{22}$-$C_{28}$ | n-butanol | 118° C. | 85 |

Total solids, DMSO insolubles and NDOM comparable to those of the previous Examples are obtained.

| GULF DEVELOPMENT CHEMICAL Carbon No. Distribution by Chromatography: % by Weight | |
|---|---|
| $C_{18}$ | 0.2 |
| $C_{20}$ | 5.1 |
| $C_{22}$ | 33.3 |
| $C_{24}$ | 26.1 |
| $C_{26}$ | 13.4 |
| $C_{28}$ | 7.6 |
| $C_{30}$ | 4.7 |
| $C_{32}$ | 3.2 |
| $C_{34}$ | 2.2 |
| $C_{36}$ | 1.7 |
| $C_{38}$ | 1.1 |
| $C_{40}$ | 0.8 |
| $C_{42}$ | 0.5 |
| $C_{44}$ | 0.1 |

It will be understood that the instant invention is capable of obvious variations and modifications without departing from its scope.

What is claimed is:

1. A process for the preparation of an alkali or alkaline earth metal or ammonium salt of an alkanesulfonic acid which comprises:
   (i) continuously and incrementally adding to a reaction mixture, under reflux, an admixture of a free radical initiator and a acyclic alpha-monoolefinic compound having a terminal double bond and containing from 5-30 carbon atoms or mixtures of said compounds, wherein said reaction mixture comprises:
      (1) a cosolvent mixture of water and an aliphatic organic hydroxyl containing compound having from 1-6 carbon atoms wherein the ratio of said organic compound to water is from 4:1 to 1:9,
      (2) an alkali or alkaline earth metal or ammonium bisulfite, and
      (3) a first portion of a free radical initiator, said first portion of free radical initiator comprising up to about 25% of the total initiator, the remainder of the free radical initiator being admixed with said monoolefin and added simultaneously therewith to said reaction mixture and wherein the ratio of said monoolefin to said bisulfite varies from about 0.1/1.6 to about 1.0/1.6, and
   (ii) upon the completion of the addition of initiator and olefin, continuing to reflux the reaction mixture, while maintaining the pH between 4 to 9 by the addition of an acid or acid-forming compound or a base until the reaction is complete.

2. A process as defined in claim 1 wherein said olefin is a branched chain compound having no branching at either the 1 or 2 carbon atom of the vinyl group.

3. A process as defined in claim 1 wherein said olefin is a straight-chain compound.

4. A process as defined in claim 1 wherein said first portion of said free radical initiator has a half life shorter than said free radical initiator which is in admixture with said olefin.

5. A process as defined in claim 1 wherein said first portion of said free radical initiator is selected from the group consisting of azobisisobutyronitrile, tertiary butyl perbenzoate and mixtures thereof and wherein the remainder of said free radical initiator is tertiary butyl perbenzoate.

6. A process as defined in claim 5 wherein said first portion of a free radical initiator in said reaction mixture is a mixture of azobisisobutyronitrile and tertiary butyl perbenzoate.

7. A process as defined in claim 1 wherein the alkali metal bisulfite is sodium bisulfite.

8. A process according to claim 1 wherein the free radical initiators are selected from the group consisting of $O_2$, $H_2O_2$, $Na_2O$, NaOCl, benzoyl peroxide, peracetic acid, t-butyl perbenzoate, 2,2-bis(t-butylperoxy)butane, di(t-butyl peroxide), ortho t-butyl perphthalate, t-butyl peroxymaleic acid, azobisisobutyronitrile.

9. The process of claim 1 wherein the alkali and alkaline earth metal bisulfites are selected from the group consisting of sodium metabisulfite, potassium bisulfite, ammonium bisulfite, calcium bisulfite and magnesium bisulfite.

10. A process according to claim 1 wherein the pH is maintained between about 6 to about 8.

11. A process according to claim 1 wherein the pH is maintained between about 6.9±0.2.

12. A process according to claim 1 wherein the reaction is conducted at a temperature of from about 50° C. to about 200° C.

13. A process according to claim 1 wherein the ratio of said alpha-monoolefinic compound to said bisulfite is from 1.0 moles of olefin to about 1.2 moles of bisulfite ion.

14. A process according to claim 1 wherein the pH is maintained by treating the reaction mixture with inorganic or organic acids selected from the group consisting of sulfuric, phosphoric, nitric and hydrochloric acids and organic fatty acids containing from 8-16 carbon atoms.

15. A process according to claim 1 wherein the acid-forming compound is $SO_2$.

16. A process for the preparation of the sodium salt of an alkanesulfonic acid wherein sodium bisulfite is prepared by dissolving about 4.2 moles of sodium metabisulfite in about 201 moles of water, adjusting the pH to about 5.5 with NaOH, then forming a reaction mixture comprising said sodium bisulfite, about 40 moles of isopropyl alcohol and about 0.05 moles of t-butyl perbenzoate and heating to reflux continuously and incrementally, adding to said reaction mixture 6.9 moles of 1:1 $C_{10}$ and $C_{14}$ acyclic straight chain alpha-monoolefins having a terminal double bond and containing about 0.15 moles of t-butyl perbenzoate, continuing the reaction, under reflux, maintaining the pH at about 6.9±0.2 by addition of $SO_2$ until the reaction is complete.

17. The process of claim 16 wherein 0.07 moles of azobisisobutyronitrile is present prior to the addition of said alpha-monoolefin.

* * * * *

UNITED STATES PATENT AND TRADEMARK OFFICE
CERTIFICATE OF CORRECTION

PATENT NO. : 4,275,013
DATED : June 23, 1981
INVENTOR(S) : Richard Tokosh et al

It is certified that error appears in the above—identified patent and that said Letters Patent is hereby corrected as shown below:

In Claim 8, line 19, change "$Na_2O$" to --$Na_2O_2$--.

Signed and Sealed this

Twenty-fourth Day of August 1982

[SEAL]

Attest:

GERALD J. MOSSINGHOFF

Attesting Officer     Commissioner of Patents and Trademarks